US012773433B2

(12) United States Patent
Lee et al.

(10) Patent No.: US 12,773,433 B2
(45) Date of Patent: Oct. 27, 2026

(54) COMPOSITION OF LACTIC ACID BACTERIUM FOR USE IN PREVENTING OR TREATING Rett SYNDROME

(71) Applicant: National Taiwan University, Taipei City (TW)

(72) Inventors: Wang-Tso Lee, Taipei City (TW); Lee Chin Wong, Taipei City (TW); Yen-Tzu Wu, Taipei City (TW); Wen-Che Tsai, Taipei City (TW); Ying-Chieh Tsai, Taipei City (TW)

(73) Assignee: National Taiwan University, Taipei (TW)

( * ) Notice: Subject to any disclaimer, the term of this patent is extended or adjusted under 35 U.S.C. 154(b) by 777 days.

(21) Appl. No.: 17/797,968

(22) PCT Filed: Feb. 6, 2020

(86) PCT No.: PCT/CN2020/074445
§ 371 (c)(1),
(2) Date: Aug. 5, 2022

(87) PCT Pub. No.: WO2021/155543
PCT Pub. Date: Aug. 12, 2021

(65) Prior Publication Data

US 2023/0035928 A1 Feb. 2, 2023

(51) Int. Cl.
*A61K 35/747* (2015.01)
*A61K 45/06* (2006.01)
*A61P 25/14* (2006.01)

(52) U.S. Cl.
CPC ............ *A61K 35/747* (2013.01); *A61K 45/06* (2013.01); *A61P 25/14* (2018.01)

(58) Field of Classification Search
CPC .. A61K 35/747; A61K 45/06; C12R 2001/25; A61P 25/14; A61P 25/02
See application file for complete search history.

(56) References Cited

FOREIGN PATENT DOCUMENTS

EP 2937424 B1 * 3/2017 ............... C12R 1/25

OTHER PUBLICATIONS

MayoClinic. Rett syndrome. https://www.mayoclinic.org/diseases-conditions/rett-syndrome/symptoms-causes/syc-20377227?p=1. 2025;1-3.*
Liu et al. Effects of Lactobacillus plantarum PS128 on Children with Autism Spectrum Disorder in Taiwan: a Randomized, Double-Blind, Placebo-Controlled Trial. Nutrients. 2019;11(4):820.*
Neul JL. The relationship of Rett syndrome and MECP2 disorders to autism. Dialogues Clin Neurosci. 2012;14(3):253-262.*
Clarkson et al. Adapting the Mullen Scales of Early Learning for a Standardized Measure of Development in Children With Rett Syndrome. Intellect Dev Disabil. 2017;55(6):419-431.*
Bendheim et al. Movement disorders. https://www.mountsinai.org/care/neurology/services/movement-disorders. 2018;1.*
Mayo. Rett syndrome. https://www.augustahealth.com/disease/rett-syndrome/. 2018;1-5.*

* cited by examiner

*Primary Examiner* — Lynn Y Fan
(74) *Attorney, Agent, or Firm* — Fox Rothschild LLP

(57) ABSTRACT

The present disclosure provides a method of preventing or treating Rett syndrome in a subject in need thereof, including administering to the subject an effective amount of *Lactobacillus plantarum* subsp. *plantarum* PS128. Also provided is a composition comprising *Lactobacillus plantarum* subsp. *plantarum* PS128 and a carrier thereof for use in preventing or treating Rett syndrome in a subject in need thereof.

12 Claims, 1 Drawing Sheet

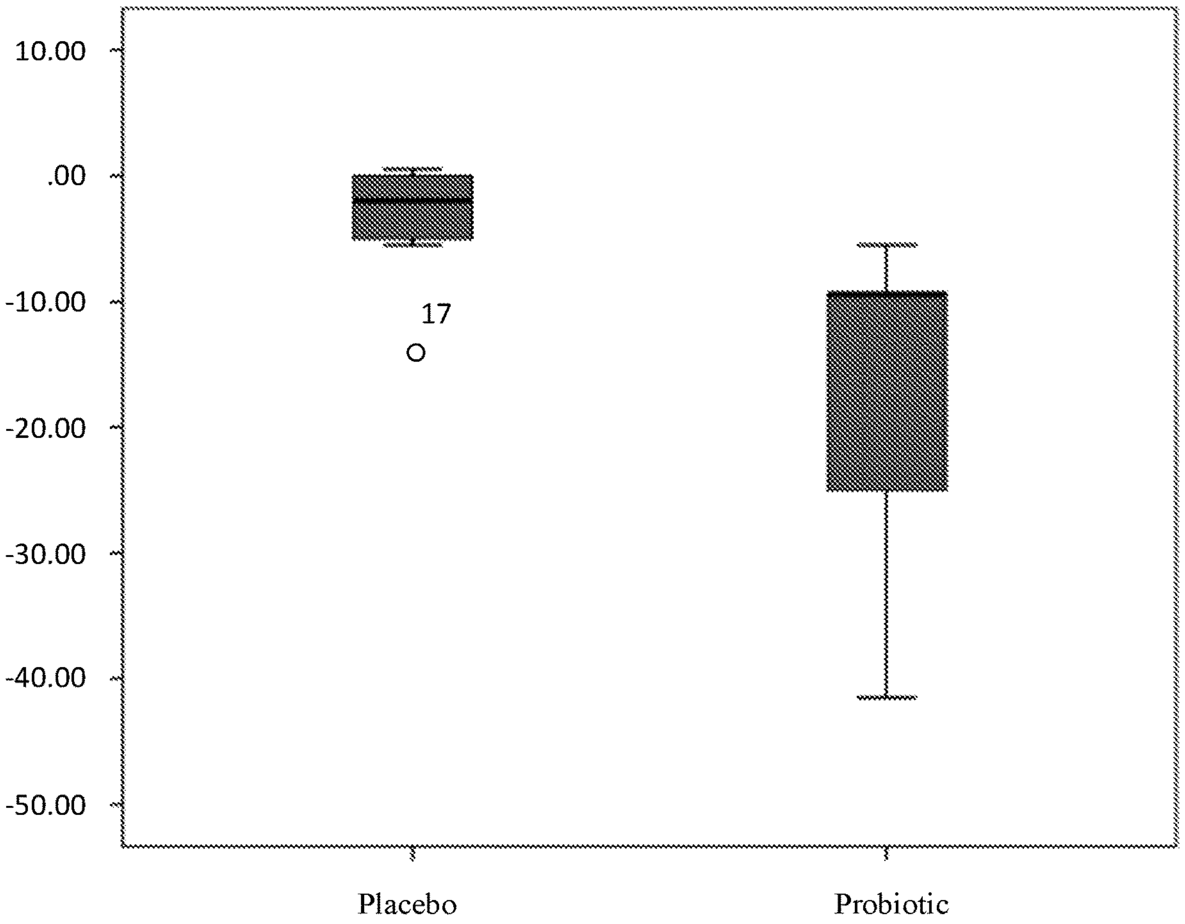
10.00
.00
-10.00
-20.00
-30.00
-40.00
-50.00
17
Placebo
Probiotic

COMPOSITION OF LACTIC ACID BACTERIUM FOR USE IN PREVENTING OR TREATING Rett SYNDROME

RELATED APPLICATION

This application is a National Phase of International Patent Application No. PCT/CN2020/074445 filed Feb. 6, 2020 the disclosures of which are incorporated herein by reference in their entirety.

BACKGROUND

1. Technical Field

The present disclosure relates to a method for preventing or treating Rett syndrome (RTT) by use of a composition comprising a lactic acid bacterium, and more particularly, to the use of *Lactobacillus plantarum* subsp. *plantarum* PS128 (PS128) for preventing or treating Rett syndrome in a subject in need thereof.

2. Description of Associated Art

Rett syndrome is a rare genetic neurological disorder that is first recognized in infancy and observed almost always in girls with a worldwide occurrence of 1 in every 10,000 female births, and even rarer in boys. Rett syndrome is usually recognized in children between 6 to 18 months as they begin to miss developmental milestones or lose abilities they had gained, although subjects affected by Rett syndrome develop normally before then. Gradually, Rett syndrome leads to severe impairments in development, beginning with loss of language skill and autistic behaviors in the early stage. During late infancy or childhood between 1 to 4 years old, the hallmark of Rett syndrome, characterized by the appearance of repetitive hand movements such as wringing, clapping, tapping, rubbing and mouthing, is the most noticeable one of diagnostic criteria. Other psychomotor manifestation includes ataxic gait, episodes of hyperventilation or apnea, and seizures that may occur in more than half of the patients. Later, patients with Rett syndrome experience motor deterioration and are characterized by progressive motor disturbances such as increased muscle tone, muscle wasting, bruxism, constipation and scoliosis. Rett syndrome can present with a wide range of disability ranging from mild to severe. The course and severity of Rett syndrome is determined by the location, type and severity of the mutation found on the methyl-CpG-binding protein 2 (MECP2) gene and X-inactivation.

The most prominent and handicapping aspect of Rett syndrome is apraxia or dyspraxia, the inability or difficulty to control the body to perform motor movements. As a result, all kinds of body movements are affected, including eye gaze and speech, making it difficult for the Rett syndrome patients to voluntarily carry out daily tasks. Furthermore, due to this apraxia or dyspraxia and their inability to speak, it may be very difficult to make an accurate assessment of intelligence in Rett syndrome patients. Most traditional testing methods for such intelligence assessment involve the use of hands and/or speech, which may be impossible for Rett Syndrome patients.

Despite the recent research into the pathogenesis and therapeutic strategy for Rett syndrome, the treatment for Rett syndrome is only palliative for now, and any reduction of psychomotor or neurological symptoms in individuals with Rett syndrome would be beneficial to the patients and their family. Currently, Rett syndrome patients are treated for symptoms such as seizures, reflux, breathing and mood, in addition to other physical and occupational therapy.

Therefore, there remains a need for a safe and effective method to prevent or treat the psychomotor or neurological symptoms related to Rett syndrome.

SUMMARY

In view of the foregoing, the present disclosure provides a method for preventing or treating Rett syndrome in a subject in need thereof, comprising administering to the subject a composition comprising an effective amount of *Lactobacillus plantarum* subsp. *plantarum* PS128 and a carrier thereof. In one embodiment, the effective amount of PS128 is at least $1\times10^9$ CFU, at least $1\times10^{10}$ CFU or at least $1\times10^{11}$ CFU, including $1\times10^9$ CFU, $2\times10^9$ CFU, $3\times10^9$ CFU, $4\times10^9$ CFU, $5\times10^9$ CFU, $6\times10^9$ CFU, $7\times10^9$ CFU, $8\times10^9$ CFU, $9\times10^9$ CFU, $1\times10^{10}$ CFU, $2\times10^{10}$ CFU, $3\times10^{10}$ CFU, $4\times10^{10}$ CFU, $5\times10^{10}$ CFU, $6\times10^{10}$ CFU, $7\times10^{10}$ CFU, $8\times10^{10}$ CFU, $9\times10^{10}$ CFU, $1\times10^{11}$ CFU, $2\times10^{11}$ CFU, $3\times10^{11}$ CFU, $4\times10^{11}$ CFU, $5\times10^{11}$ CFU, $6\times10^{11}$ CFU, $7\times10^{11}$ CFU, $8\times10^{11}$ CFU, and $9\times10^{11}$ CFU, but not limited thereto.

In one embodiment of the present disclosure, the composition is administered to the subject for at least 1 week, at least 2 weeks, at least 3 weeks, at least 4 weeks, at least 5 weeks or at least 6 weeks. In another embodiment, the composition is administered to the subject for at least 1 month, at least 2 months, at least 3 months, at least 4 months, at least 5 months or at least 6 months.

In one embodiment of the present disclosure, the method for preventing or treating Rett syndrome comprises improvement in at least one of cognition, visual reception, fine motor, receptive language, expressive language, verbal age, nonverbal age and overall mental age. In another embodiment, the cognition status is assessed by Mullen Scales of Early Learning.

In another embodiment of the present disclosure, the method for preventing or treating Rett syndrome comprises improvement of dystonia. In another embodiment, the improvement of dystonia is assessed by Fahn-Marsden Rating Scale. In a further embodiment, the method for preventing or treating Rett syndrome comprises improvement of dystonia in a subject aged less than 18 years old.

In one embodiment of the present disclosure, a method for preventing or treating Rett syndrome in a subject in need thereof is provided, comprising administering a composition comprising an effective amount of *Lactobacillus plantarum* subsp. *plantarum* PS128 and a carrier thereof for reducing one or more symptoms associated with Rett syndrome. In one embodiment of the present disclosure, the symptom associated with Rett syndrome includes, but is not limited to: behavioral abnormalities including repetitive hand movements such as wringing, clapping, tapping, rubbing and mouthing; psychomotor manifestation including ataxic gait, episodes of hyperventilation or apnea, and seizures; and motor deterioration or progressive motor disturbances such as increased muscle tone, muscle wasting, bruxism, constipation and scoliosis.

In one embodiment of the present disclosure, the composition comprising the *Lactobacillus plantarum* subsp. *plantarum* PS128 as a sole active ingredient for preventing or treating the Rett syndrome in a subject in need thereof.

In one embodiment of the present disclosure, the composition is orally administrated to the subject.

In one embodiment of the present disclosure, the method further comprising administering an additional therapy to the subject. In a further embodiment, the additional therapy is selected from the group consisting of therapy for seizures, reflux, breathing or mood, physical therapy and occupational therapy.

In one embodiment of the present disclosure, the composition is a pharmaceutical composition further comprising a pharmaceutically acceptable carrier thereof. In another embodiment of the present disclosure, the pharmaceutically acceptable carrier may be a physiologically acceptable excipient or diluent. In yet another embodiment of the present disclosure, the examples of the physiologically acceptable excipient or diluent include, but are not limited to, lactose, starch, dextrin, cyclodextrin, sodium carboxymethyl starch, carboxylated starch propionate, microcrystalline cellulose, carboxymethyl cellulose, maltodextrin and magnesium stearate.

In one embodiment of the present disclosure, a composition comprising an effective amount of *Lactobacillus plantarum* subsp. *plantarum* PS128 and a carrier thereof is provided for use in preventing or treating Rett syndrome in a subject in need thereof.

BRIEF DESCRIPTION OF THE DRAWINGS

FIG. 1 shows the differences between final evaluation and baseline of dystonia assessment using Fahn-Marsden Rating Scale in Rett syndrome subjects in probiotic and placebo groups with ages less than 18.

DETAILED DESCRIPTION OF THE EMBODIMENTS

The following embodiments are used to exemplify the present disclosure. A person of ordinary skill in the art can conceive the other advantages of the present disclosure, based on the specification of the present disclosure. The present disclosure can also be implemented or applied as described in different embodiments. It is possible to modify and/or alter the examples for carrying out this disclosure without contravening their spirit and scope, for different aspects and applications.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected in this disclosure, and in this case, the meaning of the selected terms will be described in detail in the detailed descriptions of the present disclosure. Thus, the terms used herein have to be defined based on the meaning of the terms together with the descriptions throughout the specification.

Also, when a part "includes" or "comprises" a component or a step, unless there is a particular description contrary thereto, the part can further include other components or other steps, not excluding the others.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The phrase "an effective amount" refers to the amount of an active ingredient that is required to result in a reduction, inhibition or prevention of the behavioral disorder, abnormality or symptom in the individual. An effective amount will vary, as recognized by those skilled in the art, depending on routes of administration, excipient usage, and the possibility of co-usage with other therapeutic treatment.

The term "individual" as used herein is interchangeable with "subject" and includes a single biological organism, of which a neurodevelopmental disorder may occur, including, but not limited to, animals and in particular vertebrates such as mammals and in particular human beings.

The term "condition," "disorder," or "symptom" as used herein refers to psychomotor or neurological symptoms expressed by an individual with Rett syndrome.

The term "individual in need of the treatment" refers to a person expressing or suffering from one or more symptoms related to Rett syndrome. An appropriately qualified person or physician is able to identify such an individual in need of treatment using standard behavioral testing protocols or guidelines. The same behavioral testing protocols or guidelines may also be used to determine whether there is improvement to the individual's disorders or symptoms, or determine the most effective dose of the lactic acid bacterium to be administered to an individual in need of the treatment.

The term "improvement" as used herein refers to prevention or reduction in the severity or frequency, to whatever extent, of one or more of the symptoms or abnormalities expressed by the individual diagnosed with Rett syndrome. The improvement is either observed by the individual taking the treatment themselves or by another person.

Different examples have been used to illustrate the present disclosure. The examples below should not be taken as a limit to the scope of the present disclosure.

EXAMPLE

The present disclosure examined the effects of *Lactobacillus plantarum* subsp. *plantarum* PS128 for the treatment of Rett syndrome.

Example 1: Improvement of Cognition in Rett Syndrome Subjects Supplemented with PS128

A prospective randomized, double-blind, placebo-controlled trial was conducted. The inclusion criteria were individuals diagnosed with RTT and MECP2 mutation aged between 1 to 50 years. The exclusion criteria were the consumption of antibiotics and yogurt or probiotic products four weeks prior to enrollment. Participants were required to refrain from consuming yogurt or probiotic products during the study period, but were allowed to continue their regular medications and treatments. Nonetheless, those who prescribed with antibiotics during the study period were excluded.

A total of 36 individuals between the ages of 1 and 35 years with Rett syndrome and MECP2 mutation participated in this study. They were randomly assigned to receive either placebo or PS128 according to Random permuted Blocks within Strata of 2 assignments, with PS128 and placebo arms allocated in a 1:1 ratio. Physicians, study staff, and subjects were blind to group assignment. The identity supplements were concealed by the use of a placebo that matched to the PS128 in identical capsule, packaging, labeling and schedule of administration.

*Lactobacillus plantarum* subsp. *plantarum* PS128 was isolated, and deposited under DSMZ Accession No. DSM 28632 (Bened Biomedical Co., Ltd.). The PS128 product was provided in the final form of capsules containing creamy white powder. The probiotic capsules weighed 425±25 mg and contained $3\times10^{10}$ CFU/capsule of PS128, with microcrystalline cellulose as the carrier. The placebo capsules only contained microcrystalline cellulose. All capsules were identical in taste and appearance. They were stored at a refrigerated temperature (4 to 8° C.). The PS128 or placebo were administered 1 capsule orally 12 hours apart daily to participants in treatment and placebo arms, respectively.

One of the 36 patients was not able to complete the study, and 35 patients completed the study. There were 17 patients administered placebo and 18 patients administered probiotic PS128. There were no differences in age or mutation type for the patients between groups. Table 1 below shows the demographic and clinical characteristics of the subjects at baseline.

TABLE 1

Demographic and clinical characteristics of the subjects at baseline

| | Total (n = 35) | Placebo (n = 17) | PS128 (n = 18) | P value |
|---|---|---|---|---|
| **Gender** | | | | |
| Female/male | 34/1 | 16/1 | 18/0 | |
| Age in years, mean (SD) | | 16.25 ± 8.57 | 18.39 ± 9.73 | 0.495 |
| **Disease severity** | | | | |
| Mild | 6 | 4 | 2 | 0.597 |
| Moderate | 23 | 10 | 13 | |
| Severity | 6 | 13 | 3 | |
| **Cognition, Mullen in age equivalent (month)** | | | | |
| Mental age | | 6.91 ± 4.76 | 7.00 ± 5.84 | 0.961 |
| Verbal age | | 7.35 ± 4.25 | 7.00 ± 6.16 | 0.844 |
| Nonverbal age | | 6.47 ± 5.60 | 7.00 ± 5.83 | 0.786 |
| Gross motor | | 10.06 ± 6.03 | 9.33 ± 5.74 | 0.718 |
| Visual reception | | 7.29 ± 4.63 | 7.33 ± 5.73 | 0.982 |
| Fine motor | | 5.65 ± 6.76 | 6.67 ± 6.08 | 0.643 |
| Receptive language | | 7.71 ± 4.00 | 8.06 ± 6.18 | 0.843 |
| Expressive language | | 7.00 ± 5.20 | 5.94 ± 7.85 | 0.641 |
| Vineland Adaptive Behavior Scale | | 19.47 ± 24.57 | 22.89 ± 27.26 | 0.699 |
| **Social behavior** | | | | |
| RSS[1] | | 10.94 ± 3.72 | 11.39 ± 3.33 | 0.71 |
| RSBQ[2] | | 43.18 ± 12.91 | 43.44 ± 12.08 | 0.95 |
| ADAMS[3] | | 25.24 ± 10.19 | 27.11 ± 9.93 | 0.585 |
| SSI[4] | | 22.59 ± 9.02 | 21.50 ± 8.46 | 0.716 |
| **Dystonia** | | | | |
| Fahn-Marsden Dystonia Rating Scale | | 52.82 ± 21.14 | 57.00 ± 21.58 | 0.567 |
| Unified Dystonia Rating Scale | | 56.47 ± 15.33 | 61.14 ± 13.33 | 0.345 |
| **Gastrointestinal evaluation** | | | | |
| Stool characteristics | | | | 1 |
| 1 | 7 | 3 (17.65)* | 4 (22.22)** | |
| 2 | 13 | 7 (41.18) | 6 (33.33) | |
| 3 | 12 | 6 (35.29) | 6 (33.33) | |
| 4 | 3 | 1 (5.88) | 2 (11.11) | |
| **Constipation** | | | | |
| Present | 15 | 6 (35.29)* | 9 (50.00)** | 0.591 |
| Absent | 20 | 11 (64.71) | 9 (50.00) | |

[1]RSS: Rett Severity Score
[2]RSBQ: Rett Syndrome Behaviour Questionnaire
[3]ADAMS: Anxiety, Depression, and Mood Scale
[4]SSI: Screen for Social Interaction
*Percentage in the placebo group
**Percentage in the PS128 group The difference of genotypes between the placebo and probiotic groups was analyzed using Chi-square/Fisher's exact test. The difference between ages was assessed via t-test. The Rett Syndrome Severity Scale (RSSS) is used to assess clinical severity. The RSSS is consisted of seven parameters as described in previous study (Chin Wong L, Hung P L, Jan T Y, Lee W T. Variations of stereotypies in individuals with Rett syndrome: A nationwide cross-sectional study in Taiwan. Autism research: Official Journal of the International Society for Autism Research, 2017, 10:1204-1214). The parent-completed Anxiety, Depression, and Mood Scale (ADAMS) and the Screen for Social Interaction (SSI) were used to document current autistic related behaviors. The ADAMS was used for screening anxiety, depression and mood disorders among individuals with mental retardation. The reliability and validity of the SSI total score and percentile score have been established for patients 30 to 60 months old. Early Social-Communication Scales (ESCS) was performed to measure both protodeclarative and protoimperative joint attention behaviors. For the gastrointestinal assessment, the stool characteristics and constipation were measured at baseline and at the end of study.

To assess the cognitive status of the participants, Mullen Scales of Early Learning (MSEL) and Vineland Adaptive Behavior Scales (VABS) were adopted. The measurements were obtained at baseline and at the end of study. The examiner specializing in child psychology served as the examiner for MSEL. The MSEL contains 5 subscales: Visual Reception, Expressive Language, Receptive Language, Gross Motor, and Fine Motor. It is a comprehensive norm-referenced developmental test for children aged from 0 to 68 months. Since the girls enrolled in this study were outside of the typical age range for administration of this test, performance was reported in age equivalents. A non-verbal mental age was via averaging the age equivalents from the visual reception and fine motor scales. A verbal mental age was constructed by averaging the age equivalents from the Receptive Language and Expressive Language scales. Daily adaptive functioning was measured using parent-completed VABS. Regression analysis was used to determine the treatment effect between the 2 visits. Multivariate analysis was used to control for the effect of potential confounders. Statistical significance was defined as a P-value<0.05.

As a result, the multivariable regression analysis model estimates a significant increase in overall mental age at 4 months follow-up visit by 0.77 months in the probiotic group compared to the placebo group, after adjusting to baseline mental age and age (shown below in Table 2). There were also increases in verbal and nonverbal age at follow up in probiotic compared to placebo (p=0.47 and p=0.13, respectively).

Analyzing at the individual subscales level of MSEL, there were also increases in visual reception (p=0.069), fine motor (p=0.36), expressive language (p=0.75) and receptive language (p=0.67) in probiotic compared to placebo at follow up, after adjusting to baseline and age.

TABLE 2

Regression analysis of overall mental age by Mullen Scale of Early learning (MSEL)

| | Coefficient | SE* | P value | 95% CI** |
|---|---|---|---|---|
| Baseline | 0.902 | 0.034 | 0.000 | 0.833, 0.970 |
| Age | −0.001 | 0.020 | 0.948 | −0.041, 0.039 |
| Probiotic v. placebo | 0.773 | 0.345 | 0.033 | 0.069, 1.478 |
| Constant | 0.488 | 0.498 | 0.334 | −0.527, 1.503 |

*SE: standard error
**CI: confidence interval

Example 2: Significant Improvement of Dystonia in Subjects Supplemented with PS128

The same cohort in EXAMPLE 1 was also evaluated for dystonia. Two pediatric neurologists performed dystonia assessment using Fahn-Marsden Rating Scale and Unified Dystonia Rating Scale. The higher scores indicate more severe dystonia. The measurements were obtained at baseline and at the end of study. Regression analysis was used to determine the treatment effect between the 2 visits. Multivariate analysis was used to control for the effect of potential confounders. Statistical significance was defined as a P-value<0.05.

The multivariable regression analysis model estimates a significant decrease in Fahn-Marsden Dystonia Rating Scale (F-M) by 8.78 points in the probiotic group compared to the placebo group, after adjusting to baseline score and age to assess the association between F-M score at 4 months follow-up visit (shown in Table 3 below).

TABLE 3

Regression analysis of Fahn-Marsden Dystonia Rating Scale

| | Coefficient | SE | P value | 95% CI |
|---|---|---|---|---|
| Baseline | 0.759 | 0.077 | 0.000 | 0.602, 0.917 |
| Age | 0.654 | 0.180 | 0.001 | 0.287, 1.021 |
| Probiotic v. placebo | −8.786 | 2.699 | 0.003 | −14.290, −3.282 |
| Constant | −2.414 | 3.967 | 0.547 | −10.504, 5.676 |

Example 3: Significant Improvement of Dystonia and Cognition in Subjects Supplemented with PS128

A prospective double-blind randomized controlled study for a 16-weeks period was performed to determine the effect of probiotic *Lactobacillus plantarum* (PS128) on the core clinical features of Rett syndrome. Patients with clinical diagnosis of Rett syndrome were recruited. The exclusion criteria were those who took probiotic or probiotic-related product 4 weeks prior to the study or during the study, those who took antibiotic 4 weeks prior to the study, those who showed poor compliance with any aspect of the study, and those who had adverse reactions to PS128.

A total of 34 patients having MECP2 mutations with age ranging from 1.8 to 35.8 years old completed the 4-month period trial. These subjects were randomly assigned to receive either placebo or PS128 according to Random permuted Blocks within Strata of 2 assignments, with PS128 or placebo treatment allocated in a 1:1 ratio. Physicians, study staff, and subjects were blind to group assignment.

Dystonia status was assessed using Fahn-Marsden Rating Scale and Unified Dystonia Rating Scale. Cognitive data were obtained using the Mullen Scales of Early Learning, Vineland Adaptive Behavior Scales and Early Social Communication Scales (ESCS). The Rett Syndrome Severity Scale was used to assess the effect of PS128 on clinical severity. The stool characteristics were assessed with a modified Bristol stool chart. Statistic analysis method used was the independent t-test to analyze the differences between final and baseline evaluation of each parameters.

At the end of the study, all subjects were found to tolerate well to probiotic PS128. After supplementation of probiotics, there were statistically significant improvements of dystonia in subjects having MECP2 mutations with age below 18 years (p=0.027), as shown in FIG. 1.

In addition, for the cognitive evaluation assessed by MSEL, there was regression observed in the placebo group, particularly in visual reception, fine motor and expressive language; however, such regression was not observed in the probiotic group. In contrast, the probiotic group showed improved scores in visual reception, receptive language, fine motor, and expressive language when compared to the placebo group. Table 4 and Table 5 below show the differences between final evaluation and baseline of each parameter using independent t-test in Rett syndrome with age <18 and age ≥18 between the placebo and probiotic groups.

TABLE 4

Differences between final evaluation and baseline of each parameter using independent t-test in Rett syndrome with age < 18

| Mullen Scales of Early Learning | Placebo (N = 11) | Probiotic (N = 7) | P-value |
|---|---|---|---|
| Gross Motor | 1.36 ± 3.50 | 0.86 ± 2.19 | 0.90 |
| Visual Reception | −0.55 ± 2.91 | 0.29 ± 3.40 | 0.18 |
| Fine Motor | 0.91 ± 1.45 | 0.29 ± 1.50 | 0.19 |
| Receptive Language | 0.55 ± 1.86 | 0.57 ± 2.07 | 0.75 |
| Expressive Language | −0.36 ± 2.15 | 0 ± 2.16 | 0.79 |

TABLE 5

Differences between final evaluation and baseline of each parameter using independent t-test in Rett syndrome with age ≥ 18

| Mullen Scales of Early Learning | Placebo (N = 6) | Probiotic (N = 10) | P-value |
|---|---|---|---|
| Gross Motor | 1.17 ± 2.71 | 1.00 ± 2.40 | 0.90 |
| Visual Reception | −2.00 ± 4.47 | 0.90 ± 2.42 | 0.18 |
| Fine Motor | −0.67 ± 2.58 | 1.10 ± 2.02 | 0.19 |
| Receptive Language | 1.17 ± 2.79 | 1.60 ± 2.01 | 0.75 |
| Expressive Language | −0.67 ± 3.93 | −0.10 ± 4.28 | 0.79 |

The foregoing descriptions of the detailed embodiments are only illustrated to disclose the principle and functions of the present disclosure and do not restrict the scope of the present disclosure. It should be understood to those skilled in the art that all modifications and variations according to the principle in the disclosure of the present disclosure should fall within the scope of the appended claims. It is intended that the specification and examples are considered as exemplary only, with a true scope of the disclosure being indicated by the following claims.

What is claimed is:

1. A method for treating Rett syndrome in a subject in need thereof, comprising administering a composition comprising an effective amount of *Lactobacillus plantarum* subsp. *plantarum* PS128 and a carrier thereof to the subject, wherein treating the Rett syndrome comprises improvement in at least one of cognition, visual reception, fine motor, receptive language, expressive language, verbal age, non-verbal age and overall mental age, and wherein the improvement in cognition is assessed by Mullen Scales of Early Learning.

2. The method of claim 1, wherein treating the Rett syndrome comprises improvement of dystonia.

3. The method of claim 2, wherein the subject is aged less than 18 years old.

4. The method of claim 2, wherein the improvement of dystonia is assessed by Fahn-Marsden Rating Scale.

5. The method of claim 1, wherein treating the Rett syndrome comprises reducing one or more symptoms associated with the Rett syndrome.

6. The method of claim 5, wherein the one or more symptoms associated with the Rett syndrome includes behavioral abnormality, repetitive hand movement, psychomotor manifestation, motor deterioration or progressive motor disturbance.

7. The method of claim 5, wherein the composition comprises the *Lactobacillus plantarum* subsp. *plantarum* PS128 as a sole active ingredient for reducing the one or more symptoms associated with the Rett syndrome.

8. The method of claim 1, wherein the composition is orally administrated to the subject.

9. The method of claim 1, wherein the composition is a pharmaceutical composition, and the carrier is a pharmaceutically acceptable carrier thereof.

10. The method of claim 1, wherein the composition contains at least $1\times10^9$ CFU of the *Lactobacillus plantarum* subsp. *plantarum* PS128.

11. The method of claim 1, wherein the composition is administered to the subject for at least one week.

12. The method of claim 1, further comprising administering to the subject an additional therapy selected from the group consisting of therapy for seizures, reflux, breathing or mood, physical therapy and occupational therapy.

* * * * *